(12) United States Patent
Park et al.

(10) Patent No.: US 12,426,791 B2
(45) Date of Patent: *Sep. 30, 2025

(54) BIO-INFORMATION MEASURING APPARATUS AND BIO-INFORMATION MEASURING METHOD

(71) Applicant: SAMSUNG ELECTRONICS CO., LTD., Suwon-si (KR)

(72) Inventors: Sang Yun Park, Hwaseong-si (KR); Jae Min Kang, Seoul (KR); Yong Joo Kwon, Yongin-si (KR); Youn Ho Kim, Hwaseong-si (KR); Seung Woo Noh, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 978 days.

This patent is subject to a terminal disclaimer.

(21) Appl. No.: 17/465,410

(22) Filed: Sep. 2, 2021

(65) Prior Publication Data

US 2021/0393150 A1 Dec. 23, 2021

Related U.S. Application Data

(63) Continuation of application No. 16/114,396, filed on Aug. 28, 2018, now Pat. No. 11,141,073.

(30) Foreign Application Priority Data

Sep. 13, 2017 (KR) .................... 10-2017-0116938
May 25, 2018 (KR) .................... 10-2018-0059568

(51) Int. Cl.
*A61B 5/021* (2006.01)
*A61B 5/00* (2006.01)
(Continued)

(52) U.S. Cl.
CPC ...... *A61B 5/02116* (2013.01); *A61B 5/02241* (2013.01); *A61B 5/02416* (2013.01);
(Continued)

(58) Field of Classification Search
CPC ............ A61B 5/02116; A61B 5/02241; A61B 5/02416; A61B 5/02438; A61B 5/681;
(Continued)

(56) References Cited

U.S. PATENT DOCUMENTS

| 4,461,266 A | * | 7/1984 | Hood, Jr. | ........... | A61B 5/02225 |
| | | | | | 600/490 |
| 5,857,975 A | | 1/1999 | Golub | | |

(Continued)

FOREIGN PATENT DOCUMENTS

CN 102755157 A 10/2012
CN 202723847 U 2/2013
(Continued)

OTHER PUBLICATIONS

Communication issued Aug. 30, 2022 by the China National Intellectual Property Administration in Chinese Patent Application No. 201810982329.0.

(Continued)

*Primary Examiner* — Jacqueline Cheng
*Assistant Examiner* — Tho Q Tran
(74) *Attorney, Agent, or Firm* — Sughrue Mion, PLLC

(57) ABSTRACT

An apparatus for measuring bio-information in a non-invasive manner includes: a pulse wave sensor configured to measure a plurality of pulse wave signals having different wavelengths from an object; a contact pressure sensor configured to measure contact pressure of the object while the plurality of pulse wave signals are measured; and a processor configured to obtain an oscillometric waveform based on the contact pressure and the plurality of pulse wave (Continued)

signals having the different wavelengths, and obtain bio-information based on the oscillometric waveform.

12 Claims, 22 Drawing Sheets

(51) Int. Cl.
    *A61B 5/022*     (2006.01)
    *A61B 5/024*     (2006.01)
    *A61B 5/352*     (2021.01)
(52) U.S. Cl.
    CPC .......... *A61B 5/02438* (2013.01); *A61B 5/681* (2013.01); *A61B 5/6885* (2013.01); *A61B 5/7278* (2013.01); *A61B 5/02225* (2013.01); *A61B 5/02427* (2013.01); *A61B 5/352* (2021.01); *A61B 5/6814* (2013.01); *A61B 5/7203* (2013.01); *A61B 2562/0247* (2013.01)
(58) Field of Classification Search
    CPC . A61B 5/6885; A61B 5/7278; A61B 5/02225; A61B 5/02427; A61B 5/352; A61B 5/6814; A61B 5/7203; A61B 2562/0247; A61B 5/02125; A61B 5/02141; A61B 5/0225; A61B 5/6802; A61B 5/6803; A61B 5/746
    See application file for complete search history.

(56) References Cited

U.S. PATENT DOCUMENTS

| | | | |
|---|---|---|---|
| 5,865,755 A | | 2/1999 | Golub |
| 6,045,510 A | * | 4/2000 | Ogura ................ A61B 5/02225 600/494 |
| 6,171,242 B1 | | 1/2001 | Amano et al. |
| 7,179,228 B2 | | 2/2007 | Banet |
| 7,455,643 B1 | * | 11/2008 | Li ......................... A61B 5/022 600/490 |
| 8,761,853 B2 | | 6/2014 | Thaveeprungsriporn et al. |
| 8,814,800 B2 | | 8/2014 | Fortin et al. |
| 10,034,612 B2 | | 7/2018 | Shimuta et al. |
| 10,045,700 B2 | | 8/2018 | Noh et al. |
| 10,219,752 B2 | | 3/2019 | Kang et al. |
| 10,448,848 B2 | | 10/2019 | Park et al. |
| 10,624,586 B2 | | 4/2020 | Noguchi et al. |
| 2003/0036685 A1 | | 2/2003 | Goodman |
| 2009/0326386 A1 | | 12/2009 | Sethi et al. |
| 2010/0087720 A1 | | 4/2010 | Addison |
| 2012/0283583 A1 | | 11/2012 | Batkin et al. |
| 2013/0137938 A1 | | 5/2013 | Peters |
| 2016/0113530 A1 | | 4/2016 | Nagahiro et al. |
| 2016/0198955 A1 | | 7/2016 | Fortin |
| 2016/0278645 A1 | | 9/2016 | Yoon |
| 2017/0367597 A1 | | 12/2017 | Fortin |
| 2018/0110427 A1 | | 4/2018 | Kang et al. |
| 2018/0177413 A1 | | 6/2018 | Kwon et al. |
| 2020/0000353 A1 | | 1/2020 | Park et al. |

FOREIGN PATENT DOCUMENTS

| | | |
|---|---|---|
| CN | 105286815 A | 2/2016 |
| CN | 105377137 A | 3/2016 |
| CN | 105873503 A | 8/2016 |
| CN | 106333655 A | 1/2017 |
| CN | 106419878 A | 2/2017 |
| CN | 106560155 A | 4/2017 |
| JP | 64-15028 A | 1/1989 |
| JP | 7-148125 A | 6/1995 |
| JP | 2006-263354 A | 10/2006 |
| KR | 10-0609927 B1 | 8/2006 |
| KR | 10-1210828 B1 | 12/2012 |
| KR | 10-2016-0047964 A | 5/2016 |
| KR | 10-2016-0115017 A | 10/2016 |
| KR | 10-2017-0041117 A | 4/2017 |
| KR | 10-20180076050 A | 7/2018 |
| WO | 2016/110781 A1 | 7/2016 |
| WO | 2017/152098 A1 | 9/2017 |

OTHER PUBLICATIONS

Communication issued Nov. 14, 2022 by the Korean Intellectual Property Office in Korean Patent Application No. 10-2018-0059568.

Communication dated Feb. 28, 2023, issued by the National Intellectual Property Administration of PR China in Chinese Application No. 201810982329.0.

Communication dated Dec. 5, 2018, issued by the European Patent Office in counterpart European Patent Application No. 18193964.6.

* cited by examiner

BIO-INFORMATION MEASURING APPARATUS AND BIO-INFORMATION MEASURING METHOD

CROSS-REFERENCE TO RELATED APPLICATION(S)

This application is a continuation application of U.S. application Ser. No. 16/114,396, filed Aug. 28, 2018, claims priority from Korean Patent Application No. 10-2017-0116938, filed on Sep. 13, 2017, and Korean Patent Application No. 10-2018-0059568, filed on May 25, 2018, in the Korean Intellectual Property Office, the entire disclosures of which are incorporated herein by reference in their entireties.

BACKGROUND

1. Field

Apparatuses and methods consistent with exemplary embodiments relate to bio-information measurements, and more particularly to extracting cardiovascular characteristics from the bio-information measurements without using a cuff.

2. Description of the Related Art

As a general method of extracting cardiovascular characteristics in a non-invasive manner without using a pressure cuff, a pulse wave analysis (PWA) method and a pulse wave velocity (PWV) method may be used.

The PWA method is a method of extracting cardiovascular characteristics by analyzing the shape of a photoplethysmography signal or a body surface pressure signal from peripheral part of the body, for example, fingertips, the radial artery, or the like. The blood ejected from the left ventricle causes reflection at areas of large branches, such as the renal arteries and the iliac arteries, which affects the shape of the pulse wave or body pressure wave measured at the peripheral part of the body. Thus, by analyzing the shape, arterial stiffness, vascular age, aortic pressure waveform or the like can be estimated.

The PWV method is a method of extracting cardiovascular characteristics, such as arterial stiffness or blood pressure, by measuring a pulse wave transmission time. In the method, a delay (e.g., Pulse Transit Time (PTT)) between an R-peak (e.g., left ventricular contraction interval) of an electrocardiogram (ECG) and a peak of a PPG signal is measured by measuring the ECG and PPG signals of the peripheral part of the body, and a velocity at which the blood from the heart reaches the peripheral part of the body is calculated by dividing an approximate length of the arm by the PPT.

SUMMARY

According to an aspect of an exemplary embodiment, there is provided a bio-information measuring apparatus, including: a pulse wave sensor configured to measure a plurality of pulse wave signals having different wavelengths from an object; a contact pressure sensor configured to measure contact pressure of the object while the plurality of pulse wave signals are measured; and a processor configured to obtain an oscillometric waveform based on the contact pressure and the plurality of pulse wave signals having the different wavelengths, and obtain bio-information based on the oscillometric waveform.

The pulse wave sensor may include: a first pulse wave sensor including a first light source configured to emit light of a first wavelength onto the object, and a first detector configured to measure a first pulse wave signal in response to light of the first wavelength returning from the object; and a second pulse wave sensor including a second light source configured to emit light of a second wavelength, which is different from the first wavelength, onto the object, and a second detector configured to measure a second pulse wave signal in response to light of the second wavelength returning from the object.

The first wavelength may be longer than the second wavelength; and the processor may be further configured to obtain the oscillometric waveform based on a difference signal obtained by subtracting the second pulse wave signal from the first pulse wave signal.

The processor may be further configured to normalize the plurality of pulse wave signals, and obtains the oscillometric waveform by using the normalized plurality of pulse wave signals.

The first wavelength may be longer than the second wavelength; and the processor may be further configured to obtain the oscillometric waveform based on a difference signal obtained by subtracting a differential signal of the second pulse wave signal from a differential signal of the first pulse wave signal.

The processor may be further configured to exclude a portion, where noise occurs, from the plurality of pulse wave signals based on the contact pressure.

The processor may be further configured to provide contact pressure guide information to a user while the plurality of pulse wave signals are measured.

The bio-information measuring apparatus may further include an output interface configured to provide at least one of the measured plurality of pulse wave signals, the measured contact pressure, the contact pressure guide information, and a measurement result of bio-information to the user.

The bio-information may include at least one of blood pressure, vascular age, arterial stiffness, aortic pressure waveform, vascular compliance, stress index, and degree of fatigue.

The bio-information measuring apparatus may further include a communication interface configured to transmit at least one of the plurality of pulse wave signals and the bio-information to an external device.

The pulse wave sensor may include a plurality of light sources configured to emit a light of different wavelengths onto the object, and a detector configured to measure the plurality of pulse wave signals from the light of the different wavelengths which is emitted to and then returns from the object.

The processor may include a sensor controller configured to sequentially switch on the plurality of light sources based on driving conditions of the plurality of light sources.

The bio-information measuring apparatus may further include a storage configured to store the driving conditions including at least one of a driving order and a driving time of the plurality of light sources.

The pulse wave sensor may include a light source configured to emit a light onto the object, and a plurality of detectors configured to measure the plurality of pulse wave signals from the light which is emitted to and then returns from the object.

The plurality of pulse wave signals may have different wavelengths, and at least one of the plurality of detectors may include a color filter configured to pass a predetermined wavelength band to measure the plurality of pulse wave signals of the different wavelengths.

The plurality of detectors may be disposed at different distances from the light source.

The light source may be further configured to emit a first light of a first wavelength and a second light of a second wavelength onto the object; the first wavelength may be longer than the second wavelength; the plurality of detectors may include a first detector and a second detector, and a distance between the first detector and the light source is longer than a distance between the second detector and the light source; and the processor may be further configured to obtain the oscillometric waveform based on a difference signal obtained by subtracting a second signal measured by the second detector, from a first signal measured by the first detector.

According to an aspect of another exemplary embodiment, there is provided a bio-information measuring method, including: measuring a plurality of pulse wave signals having different wavelengths from an object; measuring a contact pressure of the object while the plurality of pulse wave signals are measured; obtaining an oscillometric waveform based on the contact pressure and the plurality of pulse wave signals; and obtaining bio-information based on the oscillometric waveform.

The measuring the plurality of pulse wave signals includes: emitting a light of a first wavelength onto the object and measuring a first pulse wave signal in response to the light of the first wavelength returning from the object; and emitting a light of a second wavelength, which is shorter than the first wavelength, onto the object, and measuring a second pulse wave signal in response to the light of the second wavelength returning from the object. Further, the obtaining the oscillometric waveform may include obtaining the oscillometric waveform based on a difference signal obtained by subtracting the second pulse wave signal from the first pulse wave signal.

The obtaining the oscillometric waveform may include normalizing the plurality of pulse wave signals.

The obtaining the oscillometric waveform may include excluding a portion, where noise occurs, from the plurality of pulse wave signals based on the contact pressure.

The bio-information measuring method may further include providing contact pressure guide information to a user while the plurality of pulse wave signals are measured.

The bio-information measuring method may further include providing at least one of the plurality of pulse wave signals, the contact pressure, the contact pressure guide information, and a measurement result of the bio-information to the user.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1:
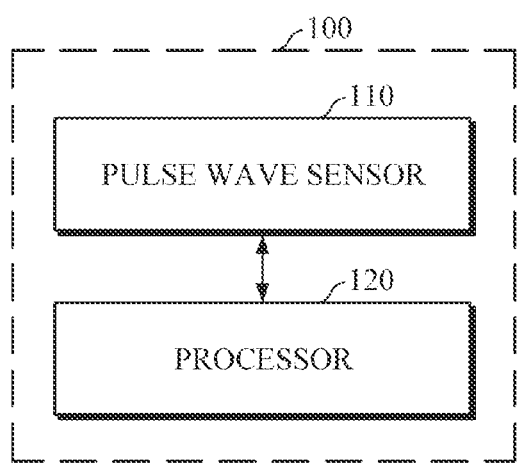
FIG. 1 is a block diagram illustrating a bio-information measuring apparatus according to an exemplary embodiment.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. Also, well-known functions or constructions are not described in detail since they would obscure the description with unnecessary detail.

It will be understood that, although the terms first, second, etc. may be used herein to describe various elements, these elements should not be limited by these terms. These terms are only used to distinguish one element from another. Any references to singular may include plural unless expressly stated otherwise. In addition, unless explicitly described to the contrary, an expression such as "comprising" or "inluding" will be understood to imply the inclusion of stated elements but not the exclusion of any other elements. Also, the terms, such as 'part' 'or module', etc., should be understood as a unit that performs at least one function or operation and that may be embodied as hardware, software, or a combination thereof.

Expressions such as "at least one of," when preceding a list of elements, modify the entire list of elements and do not modify the individual elements of the list. For example, the expression, "at least one of a, b, and c," should be understood as including only a, only b, only c, both a and b, both a and c, both b and c, or all of a, b, and c.

FIG. 1 is a block diagram illustrating a bio-information measuring apparatus according to an exemplary embodiment. The bio-information measuring apparatus 100 may be embedded in a terminal, such as a smartphone, a tablet PC, a desktop computer, and/or a laptop computer, or may be manufactured as an independent hardware device. When manufactured as an independent hardware device, the bio-information measuring apparatus 100 may be provided in the form of a wearable device, which is wearable on an object OBJ to allow easy measurement of bio-information while being carried by a user. For example, the bio-information measuring apparatus 100 may be implemented as a wristwatch-type wearable device, a bracelet-type wearable device, a wristband-type wearable device, a ring-type wearable device, a glasses-type wearable device, or a hairband-type wearable device. However, the bio-information measuring apparatus 100 is not limited thereto, and may be modified in various manners according to various purposes, including a fixed-type device used for measuring and analyzing bio-information in medical institutions.

Referring to FIG. 1, the bio-information measuring apparatus 100 includes a pulse wave sensor 110 and a processor 120.

The pulse wave sensor 110 may measure a plurality of photoplethysmography (PPG) signals (hereinafter referred to as "pulse wave signal") from an object. In this case, the object, from which pulse wave signals are measured, may be a body part which may come into contact with, or may be adjacent to, the pulse wave sensor 110, and may be a body part where pulse waves may be easily measured based on photoplethysmography (PPG) signals. For example, the object may be an area on a wrist that is adjacent to the radial artery or a top portion of the wrist through which veins or capillaries pass. In the case of measuring pulse waves on the skin surface of the wrist where the radial artery passes, the measurement may be relatively less affected by external factors, such as the thickness of a skin tissue in the wrist, which may cause errors in measurement. However, the object is not limited thereto, and may be peripheral body portions, such as fingers, toes, and the like, which have a high density of blood vessels.

The processor 120 may obtain an oscillometric waveform by using a plurality of pulse wave signals measured by the pulse wave sensor 110. In particular, the plurality of pulse wave signals may have different wavelengths from each other. However, the pulse wave signals are not limited thereto, and the oscillometric waveform may be obtained by using pulse wave signals having the same wavelength, which will be described later.

The processor 120 may measure bio-information based on the obtained oscillometric waveform. The bio-information may include blood pressure, vascular age, arterial stiffness, aortic pressure waveform, stress index, and/or degree of fatigue, but is not limited thereto. For convenience of explanation, the following description will be made by using blood pressure as an example.

For example, once a plurality of pulse wave signals are measured, the processor 120 may obtain a difference signal by subtracting a second signal, related to a pulse wave signal of a short wavelength, from a first signal related to a pulse wave signal of a relatively long wavelength among the plurality of pulse wave signals, and may obtain the oscillometric waveform based on the obtained difference signal. Its this case, the first signal may be the measured pulse wave signal of a long wavelength, or may be a differential signal obtained by differentiating the pulse wave signal of a long wavelength according to a pre-defined order of differentiation. Likewise, the second signal may be the measured pulse wave signal of a short wavelength, or may be a differential signal obtained by differentiating the pulse wave signal of a short wavelength according to a pre-defined order of differentiation. The terms "short wavelength" and "long wavelength" may indicate relative wavelengths. For example, when the pulse wave sensor 110 emits a first light having a wavelength range of 700-635 nm and a second light having a wavelength range of 560-520 nm to an object, the wavelength range of 700-635 nm and the wavelength range of 560-520 nm may be referred to as a long wavelength and a short wavelength, respectively. The pulse wave sensor 110 may receive the first light and the second light when they are reflected, deflected, or scattered from the object, and may extract the first signal and the second signal from the collected first light and second light, respectively.

Further, upon obtaining the oscillometric waveform, the processor 120 may extract feature points from the obtained oscillometric waveform, and may measure blood pressure by applying the extracted feature points to a blood pressure measurement model. For example, the processor 120 may extract a pulse wave value at a maximum peak point of the oscillometric waveform as a feature point for calculating the mean arterial pressure (MAP). Further, the processor 120 may extract pulse wave values, which are at points to the left and right of the maximum peak point and have 0.5 to 0.7 of the value at the maximum peak point, as features points for calculating the systolic blood pressure (SBP) and the diastolic blood pressure (DBP).

In this case, the blood pressure measurement model may be pre-defined as a linear function equation as represented by the following Equation 1.

$$y=ax+b \qquad \text{[Equation 1]}$$

Herein, y denotes blood pressure to be obtained, such as the DBP, the SBP, and/or the MAP, and x denotes the extracted feature point. Further, a and b denote constant values pre-calculated through preprocessing, and may be defined differently according to the types of bio-information such as the DBP, the SBP, and/or the MAP.

Figure 2A:
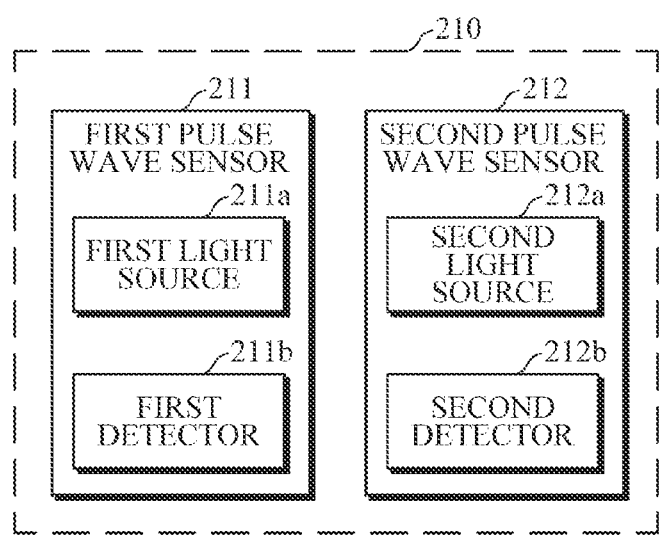
FIGS. 2A, 2B, and 2C are block diagrams illustrating a pulse wave sensor of the bio-information measuring apparatus of FIG. 1 according to an exemplary embodiment.
Figure 2B:
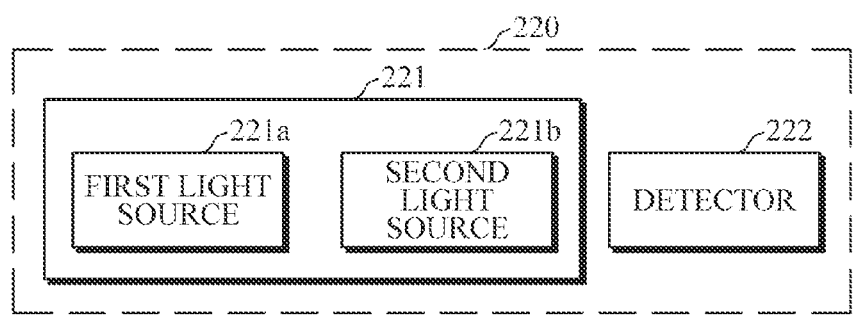
Figure 2C:
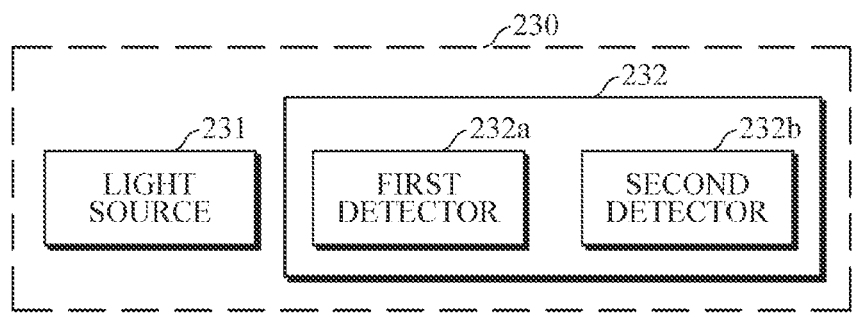

FIGS. 2A to 2C are block diagrams illustrating a pulse wave sensor of the bio-information measuring apparatus of FIG. 1 according to an exemplary embodiment. Referring to FIGS. 1 to 2C, various examples of a configuration of the pulse wave sensor 110, which measures a plurality of pulse wave signals having two or more wavelengths from an object, will be described below.

Referring to FIG. 2A, a pulse wave sensor 210 according to an exemplary embodiment may be formed as an array of pulse wave sensors to measure a plurality of pulse wave signals having different wavelengths. As illustrated in FIG. 2A, the pulse wave sensor 210 includes a first pulse wave sensor 211 and a second pulse wave sensor 212. However, this is merely exemplary for convenience of explanation, and the number of pulse wave sensors included in the pulse wave sensor array is not specifically limited.

The first pulse wave sensor 211 includes a first light source 211a which emits light of a first wavelength onto an object. Further, the first pulse wave sensor 211 includes a first detector 211b which measures a first pulse wave signal when the light having the first wavelength, is scattered or reflected from the object after being emitted by the first light source 211a onto the object.

The second pulse wave sensor 212 includes a second light source 212a which emits light of a second wavelength onto an object. Further, the second pulse wave sensor 212 includes a second detector 212b which measures a second pulse wave signal when the light having the second wavelength, is scattered or reflected from the object after being emitted by the second light source 212a onto the object.

In this case, the first light source 211a and the second light source 212a may include at least one of a light emitting diode (LED), a laser diode, and a fluorescent body, but is not limited thereto. The first detector 211b and the second detector 212b may include a photodiode.

Referring to FIG. 2B, a pulse wave sensor 220 according to another exemplary embodiment includes a light source part 221 including a first light source 221a, a second light source 221b, and a detector 222. Although FIG. 2B illustrates the light source part 221 including two light sources 221a and 221b, this is merely exemplary for convenience of explanation, and the number of light sources is not specifically limited thereto.

The first light source 221a emits light of the first wavelength onto an object, and the second light source 221 emits light of the second wavelength onto the object. In this case, the first wavelength and the second wavelength may be different from each other.

The detector 222 may measure a plurality of pulse wave signals in response to light of different wavelengths returning from the object.

For example, the first light source 221a and the second light source 221b may be driven by time-division under the control of the processor 120, to sequentially emit light onto the object. In this case, driving conditions of the light sources, including a light emission time, a driving order, a current intensity, and/or a pulse duration, of the first light source 221a and the second light source 221b may be preset. The processor 120 may control driving of each of the light sources 221a and 221b by referring to the driving conditions of the light sources.

The detector 222 may sequentially detect light of the first wavelength and light of the second wavelength, which emanate from the object after being sequentially emitted by the first light source 221 and the second light source 221b onto the object, and may measure a first pulse wave signal and a second pulse wave signal.

Referring to FIG. 2C, a pulse wave sensor 230 according to yet another exemplary embodiment includes a single light source 231 and a detector part 232. The detector part 232 includes a first detector 232a and a second detector 232b. Although FIG. 2C illustrates the detector part 231 including two detectors 232a and 232b, this is merely exemplary for convenience of explanation, and the number of detectors is not specifically limited thereto.

The single light source 231 may emit light of a single wavelength onto an object. In this case, the single light source 231 may emit light over a wide wavelength range including visible light.

The detector part 232 may measure a plurality of pulse wave signals in response to light having a single wavelength emanating from the object. To this end, the detector part 232 may have a plurality of different response characteristics.

For example, the first detector 232a and the second detector 232b may include photodiodes having different ranges of measurement so as to respond to light of different wavelengths emanating from an object. Alternatively, a color filter may be provided at a front surface of any one of the first detector 232a and the second detector 232b, or different color filters may be provided at the front surface of the two detectors, so that the first detector 232a and the second detector 232b may respond to light of different wavelengths emanating from an object.

The first detector 232a and the second detector 232b may be disposed at different distances from the single light source 231, and one detector disposed at a relatively short distance from the single light source 231 may detect light having a short wavelength, and the other detector disposed at a relatively long distance from the single light source 231 may detect light having a long wavelength. Alternatively, the first detector 232a and the second detector 232b, which are disposed at different distances from the single light source 231 may detect light of the same wavelength. In this case, according to distances of the detectors from the single light source 231, a penetration depth of light, detected by each of the detectors, into the body may be determined.

Referring to FIGS. 2A to 2C, exemplary embodiments of the pulse wave sensors for measuring pulse wave signals of different wavelengths are described above. The pulse wave sensors are not limited thereto, and various embodiments of obtaining pulse wave signals by differentiating signals according to source depths of pulse waves are also possible.

Figure 3:
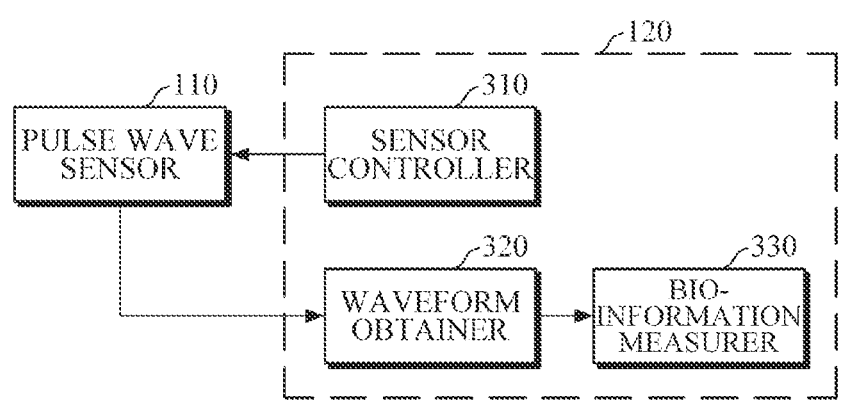
FIG. 3 is a block diagram illustrating a processor of the bio-information measuring apparatus of FIG. 1 according to an exemplary embodiment.

FIG. 3 is a block diagram illustrating a processor of the bio-information measuring apparatus of FIG. 1 according to an exemplary embodiment.

Referring to FIG. 3, the processor 120 includes a sensor controller 310, a waveform obtainer 320, and a bio-information measurer 330.

The sensor controller 310 controls a pulse wave sensor 110 to measure a plurality of pulse wave signals to obtain bio-information. The sensor controller 310 may receive a request for measuring bio-information from a user. Upon receiving the request for measuring bio-information, the sensor controller 310 may control the pulse wave sensor 110 by generating a control signal for controlling the pulse wave sensor 110. Sensor driving conditions for controlling the pulse wave sensor may be pre-stored in a storage device. Further, the sensor driving conditions may be defined for each pulse wave sensor. Upon receiving the request for measuring bio-information, the sensor controller 310 may control the pulse wave sensor by referring to the sensor driving conditions stored in the storage device. In particular, the sensor driving conditions may include a light emission time, a driving order, a current intensity, and/or a pulse duration of each light source.

Upon receiving a plurality of pulse wave signals from the pulse wave sensor 110, the waveform obtainer 320 may obtain an oscillometric waveform by using the received plurality of pulse wave signals. For example, the waveform obtainer 320 may obtain the oscillometric waveform based on a first signal related to a pulse wave signal of a long wavelength, and a second signal related to a pulse wave signal of a short wavelength, among the plurality of pulse wave signals. In this case, the first signal or the second signal may be the measured pulse wave signals of a long wavelength or a short wavelength, may be a differential signal of each pulse wave signal, or may be various other modified signals.

For example, once the plurality of pulse wave signals are measured, the waveform obtainer 320 may obtain the oscillometric waveform based on a difference signal obtained by subtracting a pulse wave signal of a short wavelength from a pulse wave signal of a long wavelength. In this case, the waveform obtainer 320 may normalize the measured plurality of pulse wave signals, and may obtain the oscillometric waveform by using the normalized pulse wave signals.

In another example, once the plurality of pulse wave signals are measured, the waveform obtainer 320 may differentiate the plurality of pulse wave signals to obtain each differential signal, and may subtract a differential signal of a short wavelength from a differential signal of a long wavelength to obtain the oscillometric waveform based on the subtracted differential signal. In this case, the order of differentiation, including a first order, a second order, . . . , an n-th order, and the like, is not specifically limited, and may be pre-defined according to the types of bio-information or various other criteria.

The bio-information measurer 330 may measure bio-information by using the oscillometric waveform obtained by the waveform obtainer 320. For example, once the oscillometric waveform is obtained, the bio-information measurer 330 may extract feature points from the oscillometric waveform, and may measure blood pressure by applying the extracted feature points to a blood pressure measurement model represented by the aforementioned Equation 1. For example, the bio-information measurer 330 may extract a pulse wave value at a maximum peak point of the oscillometric waveform as a feature point for calculating the mean arterial pressure (MAP), and may extract pulse wave values, which are at points to the left and right of the maximum peak point and have 0.5 to 0.7 of the value at the maximum peak point, as features points for calculating the systolic blood pressure (SBP) and the diastolic blood pressure (DBP).

Figure 4A:
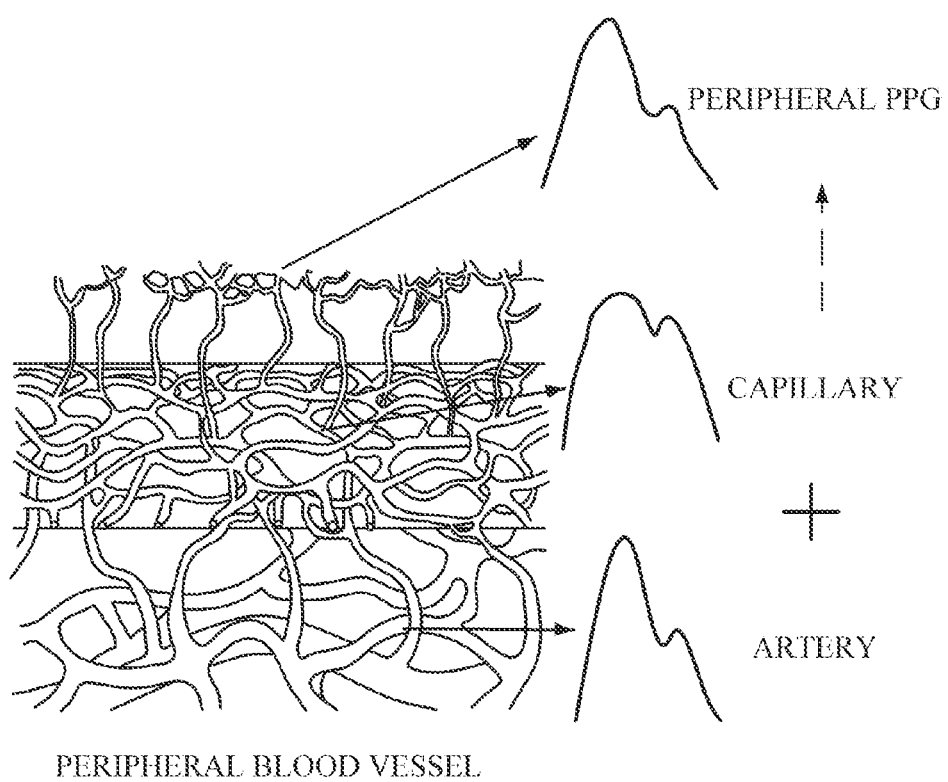
FIGS. 4A and 4B are diagrams explaining an example of general measurement of bio-information.
Figure 4B:
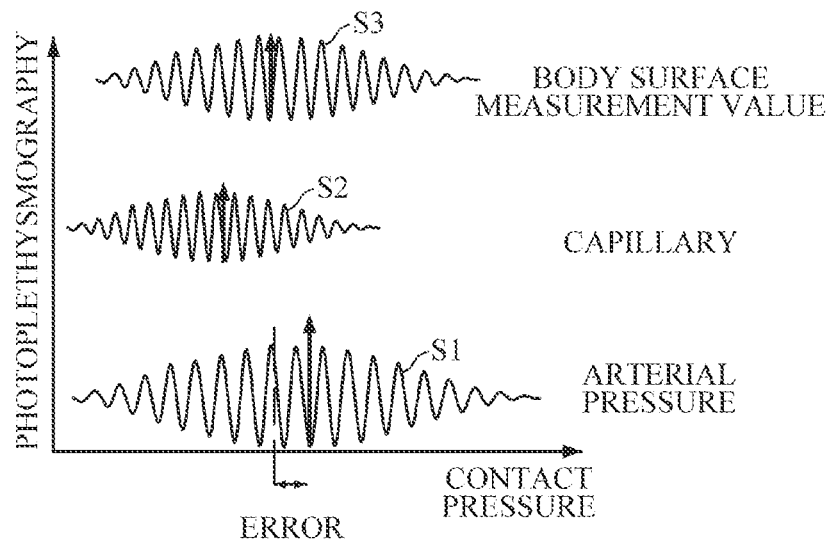

FIGS. 4A and 4B are diagrams explaining an example of general measurement of bio-information Referring to FIG. 4A, a blood pressure measuring apparatus without a cuff generally measures blood pressure by using photoplethysmography (PPG) signals. In this case, the pulse wave sensor comes into contact with a body surface at various pressure levels, and the pulse wave sensor may estimate blood pressure by measuring pulse wave signals at each contact pressure level, and by obtaining mean arterial pressure (MAP) of local blood vessels. In this case, the photoplethysmography (PPG) signals measured by the pulse wave sensor from the body surface may be observed as a combination of arterial pulse wave signals generated at great depths from the body surface and capillary pulse wave signals generated at relatively shallow depths from the body surface. Here, the capillary pulse wave signals may act as noise in estimating blood pressure using oscillometry.

Referring to FIG. 4B, a pulse wave signal at the bottom of the graph represents an arterial pulse wave signal S1; a pulse wave signal at the center of the graph represents a capillary pulse wave signal S2; and a pulse wave signal at the top of the graph represents a peripheral pulse wave signal S3. As the peripheral pulse wave signal S3 is represented by a combination of the arterial pulse wave signal S1 and the capillary pulse wave signal S2, it can be seen that a maximum amplitude point associated with blood pressure is moved from an arrow point of the arterial pulse wave signal S1 to an arrow point of the peripheral pulse wave signal S3. This shows that accuracy may be reduced when blood pressure is measured using oscillometry. That is, a body surface measurement value includes an error value added to an arterial blood pressure value, thereby resulting in a difference from accurate blood pressure values.

Figure 5A:
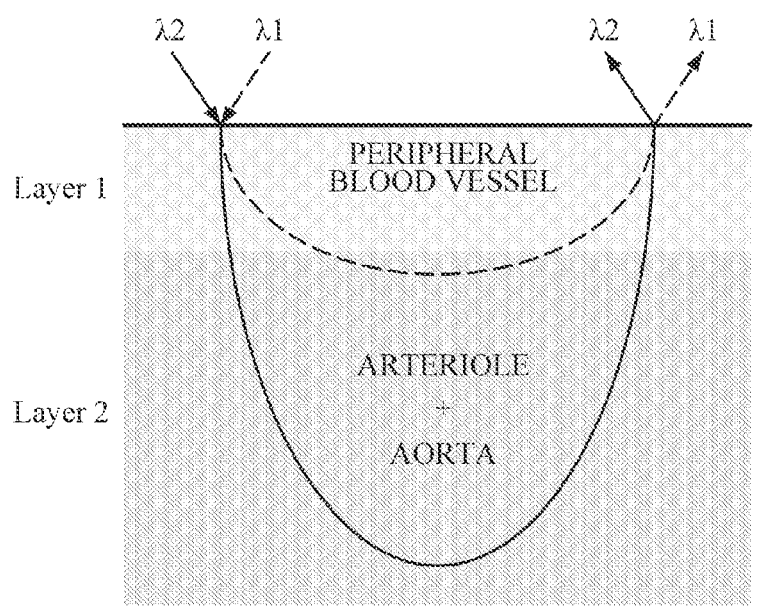
FIGS. 5A and 5B are diagrams explaining a penetration depth from a body surface according to wavelengths.
Figure 5B:
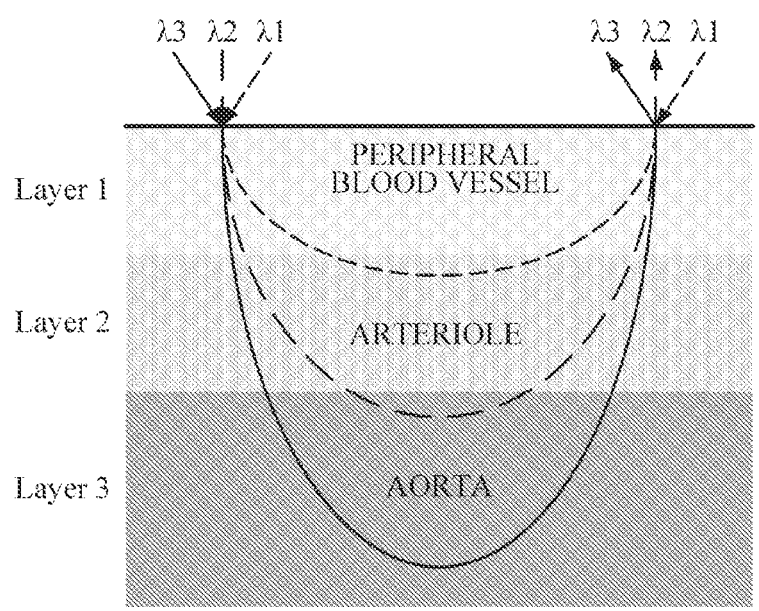

FIGS. 5A and 5B are diagrams explaining a penetration depth from a body surface according to wavelengths.

Referring to FIGS. 5A and 5B, the penetration depth from a skin surface is different according to wavelengths of light emitted from a light source onto the skin. A pulse wave signal (e.g., infrared (IR) pulse wave signal) having long wavelengths $\lambda 2$ and $\lambda 3$ may include both an arterial pulse wave signal and a capillary pulse wave signal. Further, a pulse wave signal (e.g., Green pulse wave signal) having a short wavelength $\lambda 1$ may include only the capillary pulse wave signal. In the exemplary embodiment, the arterial pulse wave signal may be recovered by using the pulse wave signal having the long wavelengths $\lambda 2$ and $\lambda 3$ and the pulse wave signal having the short wavelength $\lambda 1$, thereby improving accuracy of estimating blood pressure using oscillometry.

FIGS. 6A to 6D are diagrams illustrating bio-information measurements according to according to an exemplary embodiment. Referring to FIGS. 1 to 6D, an example where the bio-information measuring apparatus 100 measures bio-information will be described below.

Figure 6A:
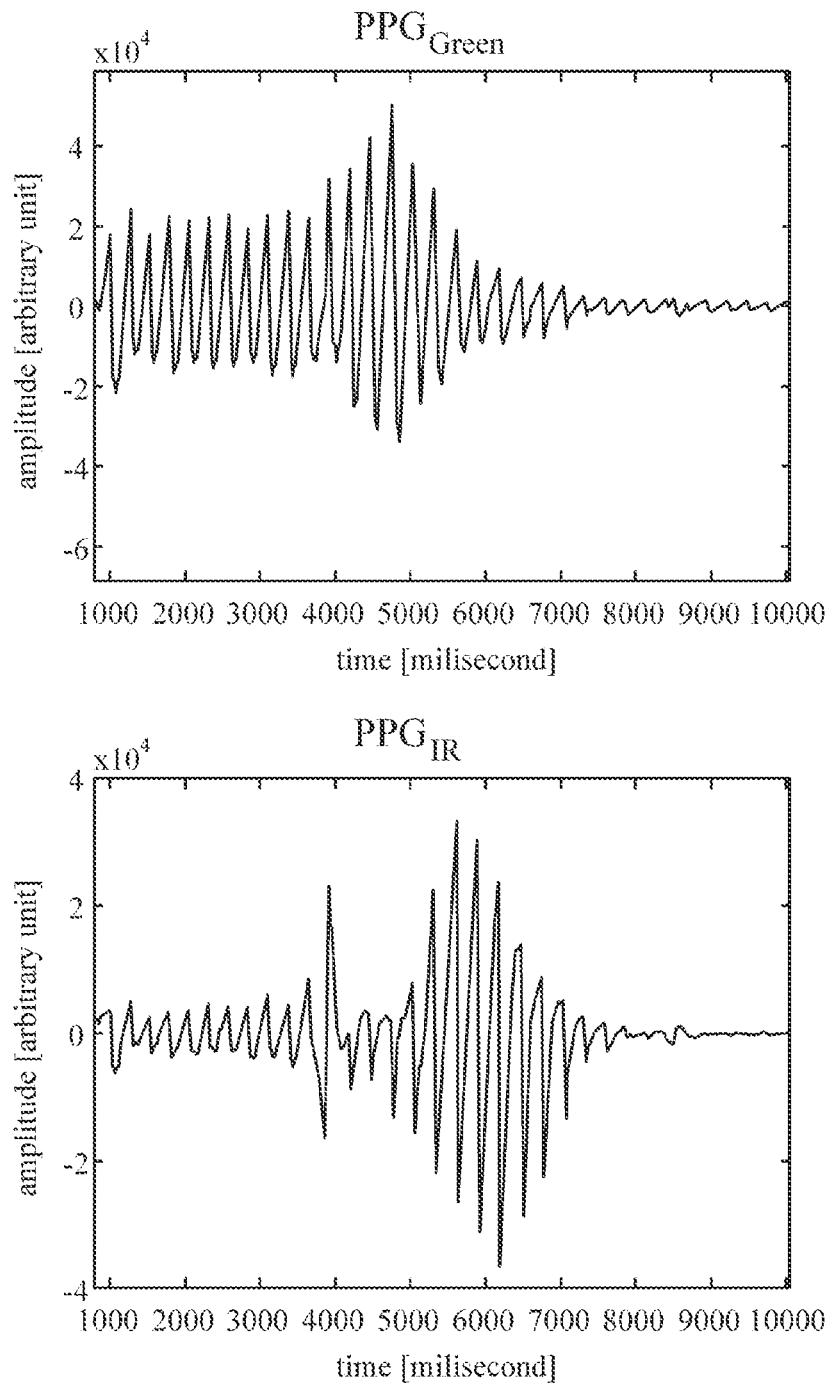
FIGS. 6A, 6B, 6C, and 6D are diagrams illustrating bio-information measurements according to according to an exemplary embodiment.

FIG. 6A illustrates an example where the bio-information measuring apparatus 100 obtains two pulse wave signals $PPG_{Green}$ and $PPG_{IR}$ having different wavelengths from an object. In this case, the pulse wave signal $PPG_{Green}$ having a relatively short wavelength includes a capillary pulse wave signal, and the pulse wave signal $PPG_{IR}$ having a relatively long wavelength includes the capillary pulse wave signal and the arterial pulse wave signal which overlap each other. For example, as described above with reference to FIGS. 2A to 2C, the bio-information measuring apparatus 100 may include various pulse wave sensors to obtain pulse wave signals of different wavelengths.

Figure 6B:
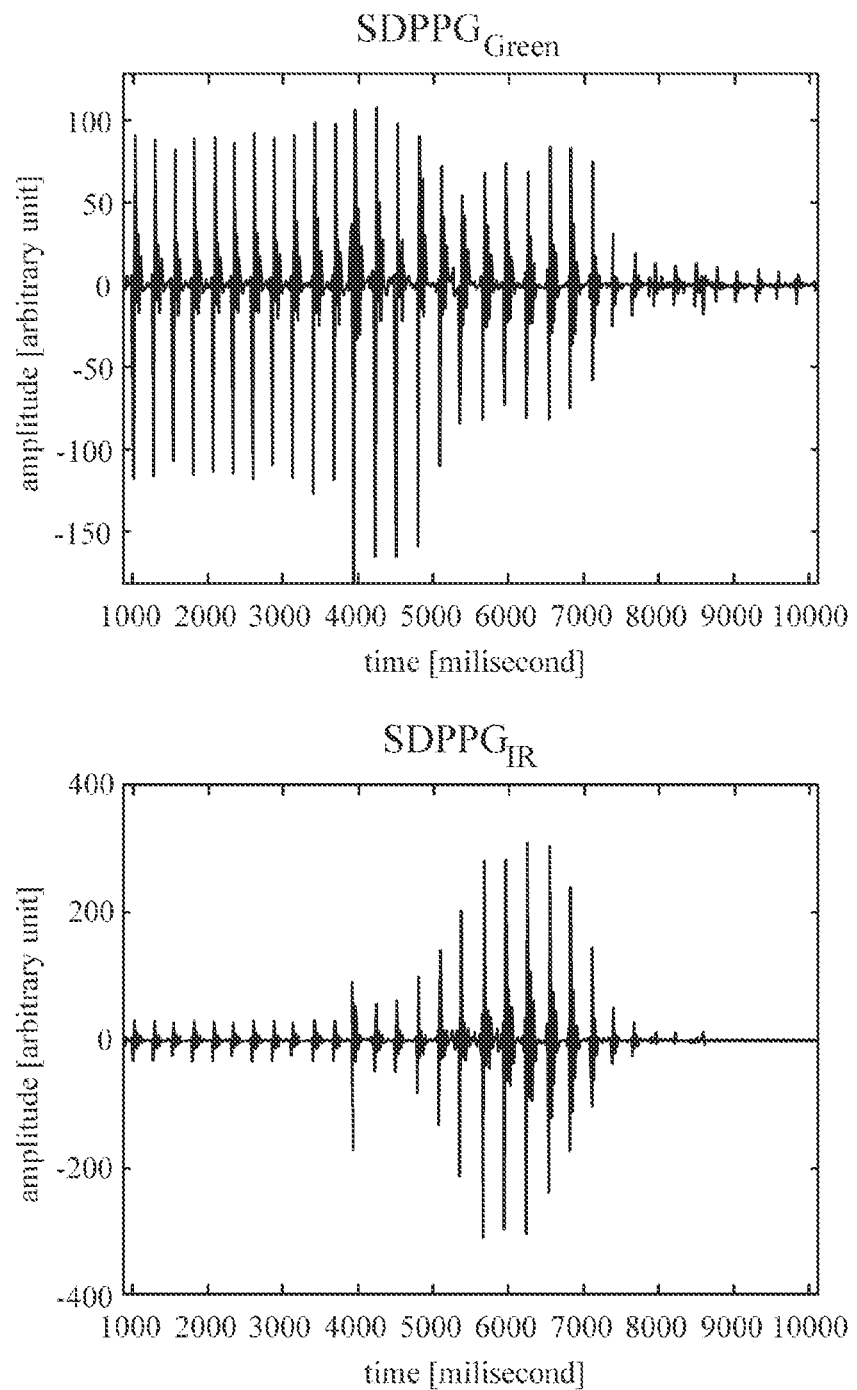

FIG. 6B illustrates an example where the bio-information measuring apparatus 100 differentiates the two obtained pulse wave signals $PPG_{Green}$ and $PPG_{IR}$ having different wavelengths to obtain quadratic differential signals $SDPPG_{Green}$ and $SDPPG_{IR}$. In this case, the bio-information measuring apparatus 100 may normalize the two obtained pulse wave signals $PPG_{Green}$ and $PPG_{IR}$, and may obtain each quadratic differential signal from the normalized pulse wave signals. Alternatively, upon obtaining the quadratic differential signals, the bio-information measuring apparatus 100 may normalize the obtained quadratic differential signals. The quadratic differential signals, having acceleration dimension, may be similar to pressure pulse waves.

Figure 6C:
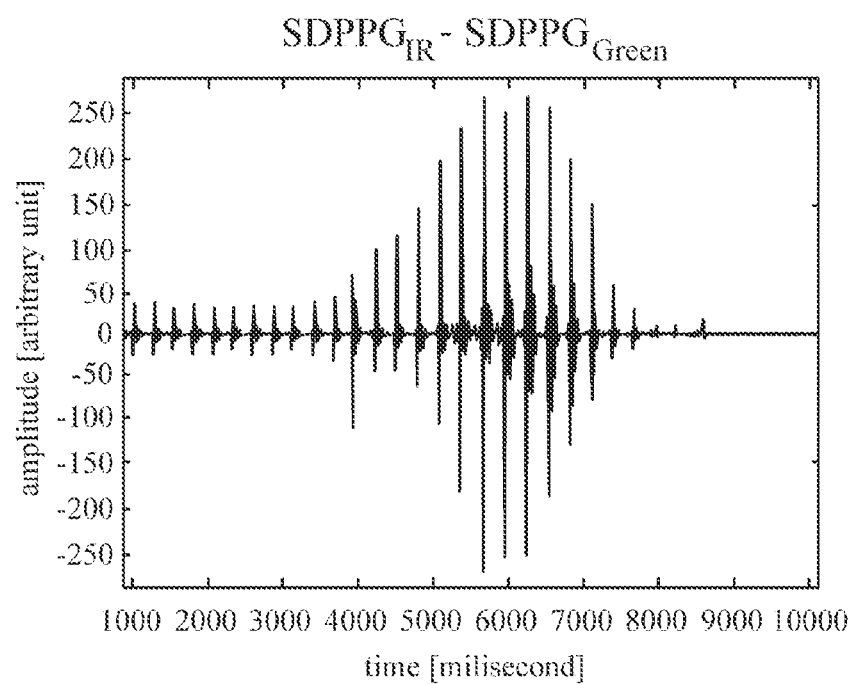

FIG. 6C illustrates an example where the bio-information measuring apparatus 100 subtracts a differential signal $SDPPG_{Green}$ having a short wavelength from a differential signal $SDPPG_{IR}$ having a relatively long wavelength, among the two obtained differential signals, to obtain a subtracted differential signal.

Figure 6D:
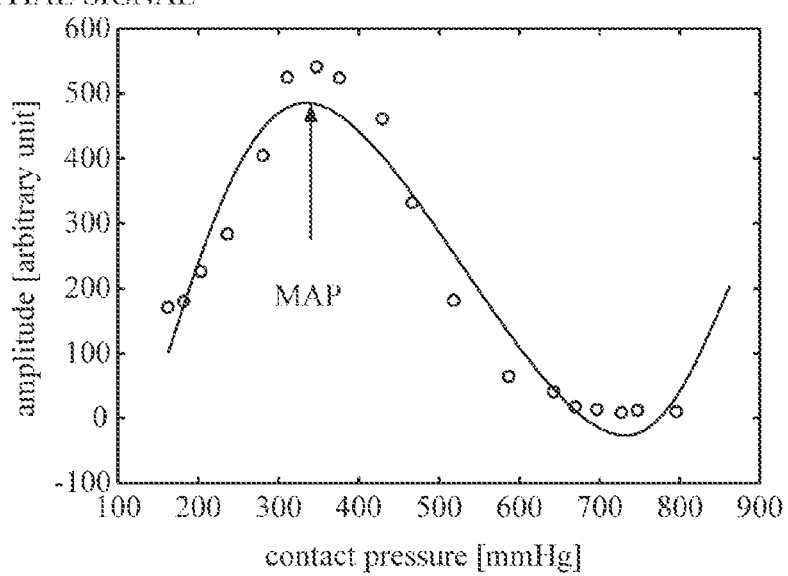

FIG. 6D illustrates an example where the bio-information measuring apparatus 100 obtains an oscillometric waveform by using the obtained subtracted differential signal and contact pressure. In this case, the contact pressure may be measured from an object at the same time when pulse wave signals are measured. For example, by using an envelope of a subtracted differential signal waveform, the bio-information measuring apparatus 100 may extract a peak-to-peak point of the subtracted differential signal waveform by subtracting a negative value from a positive value of the waveform at each measurement time. Further, the bio-information measuring apparatus 100 may obtain the oscillometric waveform by plotting the peak-to-peak point of the subtracted differential signal waveform based on a contact pressure value.

Upon obtaining the oscillometric waveform, the bio-information measuring apparatus 100 may measure blood pressure by extracting feature points from the obtained oscillometric waveform. For example, the bio-information measuring apparatus 100 may extract a contact pressure value at a maximum peak point of the oscillometric waveform or a pulse wave value of a difference signal as feature points for measuring the mean arterial pressure (MAP). Further, the bio-information measuring apparatus 100 may extract values, which are at points to the left and right of the maximum peak point and have 0.5 to 0.7 of the value at the maximum peak point, as features points for measuring the systolic blood pressure (SBP) and the diastolic blood pressure (DBP). In addition, upon extracting the feature points for the MAP, the SBP, and the DBP, the bio-information measuring apparatus 100 may apply the extracted feature points to a blood pressure estimation equation to measure each blood pressure.

Figure 7A:
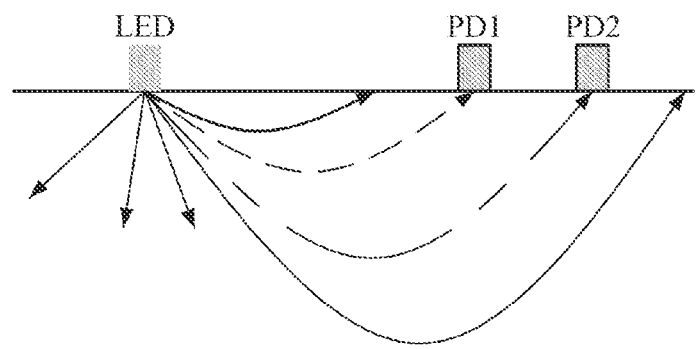
FIGS. 7A and 7B are diagrams illustrating bio-information measurements according to another exemplary embodiment.
Figure 7B:
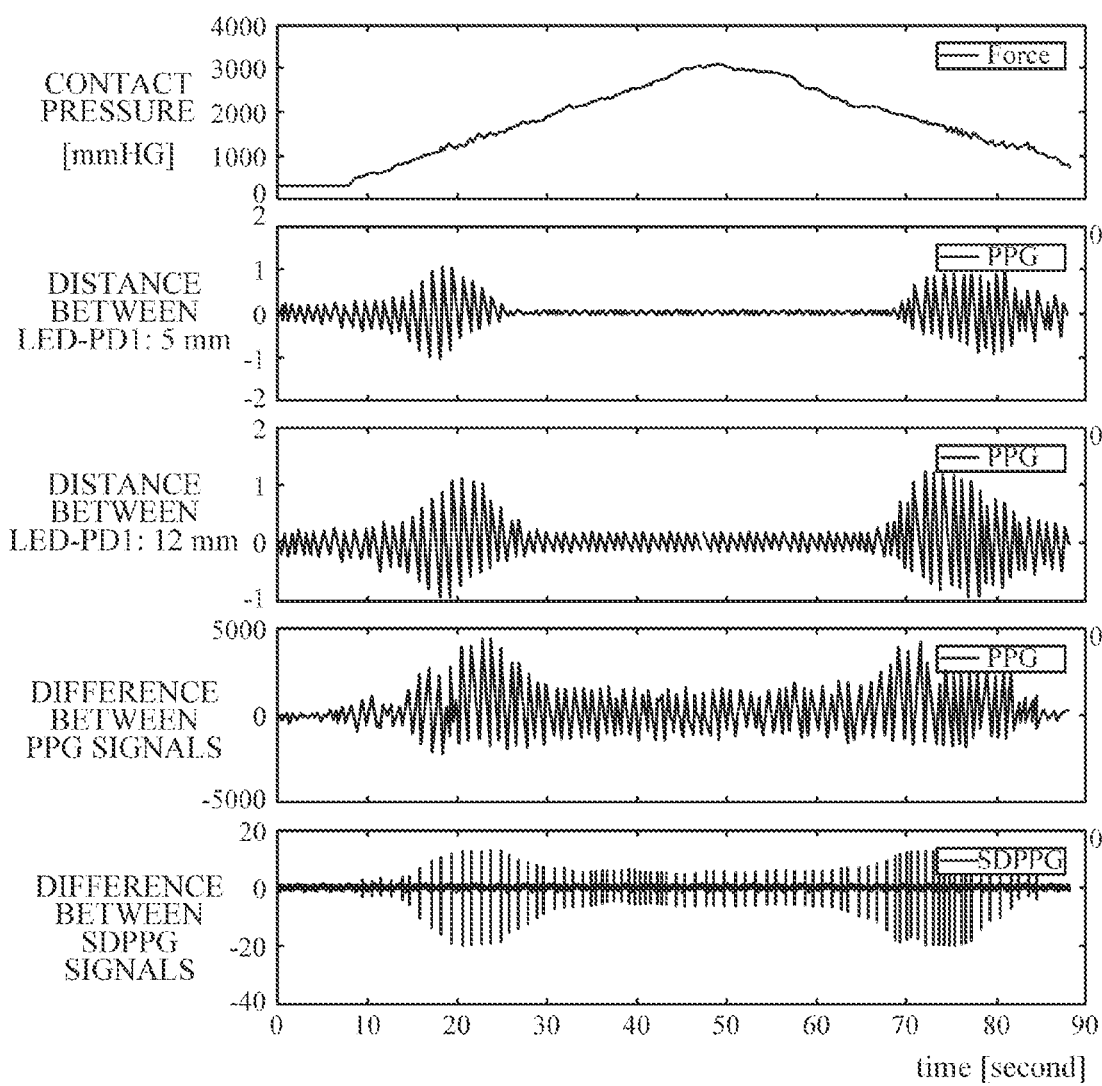

FIGS. 7A and 7B are diagrams explaining measurements of a plurality of wavelengths according to another exemplary embodiment.

Referring to FIGS. 1, 7A, and 7B, the pulse wave sensor 110 of the bio-information measuring apparatus 100 according to an embodiment includes a single light source (LED) which emits light of the same wavelength onto an object, and two or more detectors PD1 and PD2 disposed at different distances from the light source (LED). For example, the first detector PD1 may be disposed at a position 5 mm apart from the light source (LED), and the second detector PD2 may be disposed at a position 12 mm apart from the light source (LED).

Once the light source (LED) emits light of the same wavelength onto the object, light of the same wavelength scattered from the object enters into the first detector PD1 and the second detector PD2, to be detected by the first detector PD1 and the second detector PD2. In this case, according to the distances of the first detector PD1 and the second detector PD2 from the light source (LED), a penetration depth of light, detected by the first detector PD1 and the second detector PD2, into the body may be determined.

In other words, even when the light source (LED) emits light of the same wavelength, the first detector PD1, which is disposed at a relatively short distance from the light source (LED), may measure a capillary pulse wave signal or a peripheral pulse wave signal, which passes through a position relatively closer to a surface of the body, e.g., the capillary or a body surface. Further, the second detector PD2, which is disposed at a relatively long distance from the light source (LED), may measure an arterial pulse wave signal, which passes through a position deep in the body, e.g., the artery.

The bio-information measuring apparatus 100 may measure bio-information based on the first signal, related to the pulse wave signal measured by the first detector PD1, and the second signal related to the pulse wave signal measured by the second detector PD2. For example, as described above, the bio-information measuring apparatus 100 may obtain an oscillometric waveform by using a difference signal, obtained by subtracting the first signal, measured at a position relatively closer to a surface of the body, from the second signal measured at a position deep in the body, and may measure bio-information based on the obtained oscillometric waveform. In this case, the first signal may be a first pulse wave signal detected by the first detector, or a differential signal of the first pulse wave signal; and the second signal may be a second pulse wave signal detected by the second detector, or a differential signal of the second pulse wave signal. However, the signals are not limited thereto, and various modified signals may be used.

Figure 8:
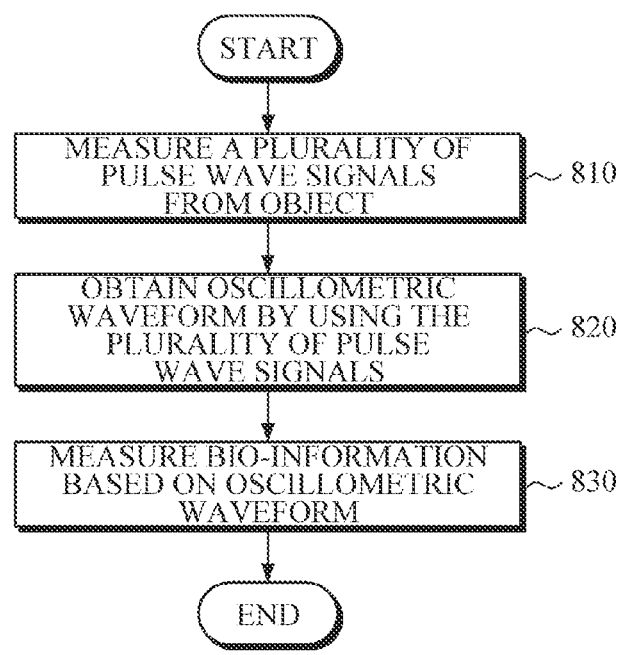
FIG. 8 is a flowchart illustrating a bio-information measuring method according to an exemplary embodiment.

FIG. 8 is a flowchart illustrating a bio-information measuring method according to an exemplary embodiment.

The bio-information measuring method of FIG. 8 may be an example of a bio-information measuring method performed by the bio-information measuring apparatus of FIG. 1. Various embodiments of the bio-information measuring method are described above with reference to FIGS. 1 to 7B, such that description thereof will be made briefly below.

In response to a request for measuring bio-information, the bio-information measuring apparatus 100 measures a plurality of pulse wave signals from an object in operation 810. The request for measuring bio-information may be received from a user. However, the request for measuring bio-information is not limited thereto, and may be automatically generated by the bio-information measuring apparatus 100 when a predetermined criterion is satisfied. For example, the bio-information measuring apparatus 100 may automatically generate a control signal for the bio-information measuring request at predetermined intervals or when a measurement result of bio-information requires to re-measure bio-information. The plurality of pulse wave signals may be pulse wave signals having different wavelengths. Various embodiments of the pulse wave sensors for measuring pulse wave signals of different wavelengths are described above.

Then, the bio-information measuring apparatus 100 may obtain an oscillometric waveform by using the measured plurality of pulse wave signals in operation 820. For example, upon measuring the plurality of pulse wave signals, the bio-information measuring apparatus 100 may obtain a difference signal by subtracting a pulse wave signal of a short wavelength from a pulse wave signal of a relatively long wavelength among the measured plurality of pulse wave signals, and may obtain the oscillometric waveform based on the obtained difference signal. In this case, the bio-information measuring apparatus 100 may normalize the measured plurality of pulse wave signals if necessary, and may obtain a difference signal by using the normalized pulse wave signals. Alternatively, the bio-information measuring apparatus 100 may differentiate the measured plurality of pulse wave signals to obtain each differential signal, and may obtain a difference signal by using the obtained differential signals. In this case, the differential signal may be a quadratic differential signal, but is not limited thereto.

Subsequently, the bio-information measuring apparatus 100 may measure bio-information based on the obtained oscillometric waveform in operation 830. For example, the bio-information measuring apparatus 100 may extract a maximum peak point of the oscillometric waveform as a feature point, and may measure bio-information by using the extracted feature point.

Figure 9:
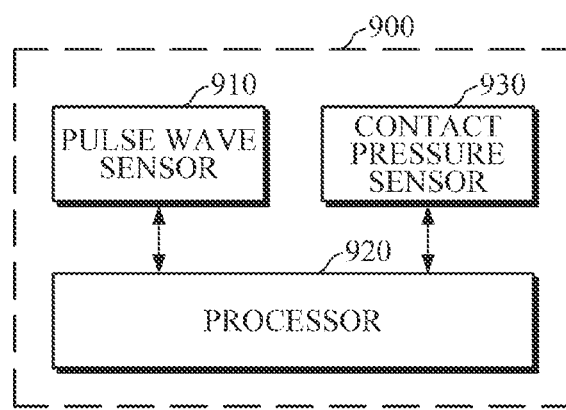
FIG. 9 is a block diagram illustrating a bio-information measuring apparatus according to another exemplary embodiment.
Figure 10:
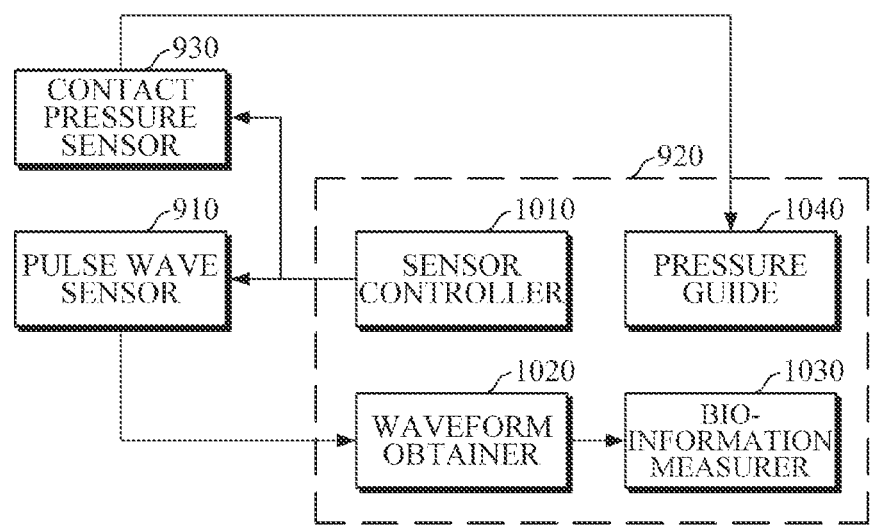
FIG. 10 is a block diagram illustrating a processor of the bio-information measuring apparatus of FIG. 9 according to an exemplary embodiment.

FIG. 9 is a block diagram illustrating a bio-information measuring apparatus according to another exemplary embodiment. FIG. 10 is a block diagram illustrating a processor of the bio-information measuring apparatus of FIG. 9 according to an exemplary embodiment.

Referring to FIG. 9, the bio-information measuring apparatus 900 includes a pulse wave sensor 910, a processor 920, and a contact pressure sensor 930. Referring to FIG. 10, the processor 920 includes a sensor controller 1010, a waveform obtainer 1020, a bio-information measurer 1030, and a pressure guide 1040.

Once a request for measuring bio-information is received, the sensor controller 1010 may generate a control signal for the pulse wave sensor 910 and the contact pressure sensor 930 to measure a pulse wave signal and a contact pressure value respectively from an object.

The pressure guide 1040 may provide contact pressure guide information for guiding pressure to be increased or decreased by a user for the pulse wave sensor 910 while pulse wave signals are measured. The pressure guide 1040 may visually display the contact pressure guide information, or may display the information using non-visual methods such as voice and/or vibration.

The contact pressure guide information may be provided before and after, or at the same time as the time when the pulse wave sensor 910 starts to measure the pulse wave signals. The contact pressure guide information may be provided continuously while the pulse wave sensor 910 measures the pulse wave signals from an object. The contact pressure guide information may be predetermined for each user based on user characteristics including a user's age, gender, health state, and/or a contact portion between the pulse wave sensor 910 and the object. The contact pressure guide information may be a contact pressure value to be increased or decreased by a user for the pulse wave sensor 910, but is not limited thereto, and may include a user's action information to induce a change in pressure applied by the object to the pulse wave sensor 910.

The pulse wave sensor 910 may measure a plurality of pulse wave signals from an object while a user changes contact pressure between the pulse wave sensor 910 and the object according to the contact pressure guide information. In this case, the plurality of pulse wave signals may be pulse wave signals of different wavelengths. The configuration of the pulse wave sensor 910 to obtain pulse wave signals of different wavelengths is described above with reference to FIGS. 2A to 2C.

While the pulse wave sensor 910 measures the pulse wave signals, the contact pressure sensor 930 may measure contact pressure between the pulse wave signal 910 and the object. For example, the contact pressure sensor 930 may be provided as a single module or an array of a plurality of modules. Further, the contact pressure sensor 930 may include a force sensor and a contact area measuring sensor, or a force sensor and a capacitive sensor array, but the contact pressure sensor 930 is not specifically limited to any one of the sensors.

The pressure guide 1040 may continuously receive contact pressure measurement values from the contact pressure sensor 930, and may provide contact pressure guide information to a user based on the received contact pressure measurement values. For example, the processor 920 may provide the contact pressure guide information based on a difference between a contact pressure measurement value measured at a specific time and a contact pressure value to be applied by a user to the pulse wave sensor 910.

The waveform obtainer 1020 may receive the plurality of pulse wave signals and the contact pressure signals which are measured for a predetermined period of time, and may measure bio-information by using the received plurality of pulse wave signals and contact pressure signals. As described above in detail, the waveform obtainer 1020 may obtain a difference signal between the plurality of pulse wave signals, and may obtain an oscillometric waveform by using the difference signal and the contact pressure signal.

In addition, the waveform obtainer 1020 may determine a portion, where noise occurs in the measured pulse wave signals, based on the contact pressure measured by the contact pressure sensor 930. For example, when compared to contact pressure to be applied by a user at a specific time or section while the pulse wave signals are measured, in the case where the contact pressure measured by the contact pressure sensor 930 falls outside a predetermined range, the waveform obtainer 1020 may determine that motion noise occurs. Alternatively, the waveform obtainer 1020 may analyze the measured pulse wave signals, and may determine an abnormal section, in which the pulse wave signals do not show a normal pattern, to be a portion where motion noise occurs. Moreover, in the case where the bio-information measuring apparatus 900 includes an acceleration sensor, the bio-information measuring apparatus 900 may determine a time or a section, where there is a sudden change in acceleration signal while the pulse wave signals are measured, to be a portion where motion noise occurs. As described above, the waveform obtainer 1020 may exclude the portion, where motion noise occurs, from the pulse wave signal or contact pressure signal, and may obtain an oscillometric waveform by using other portions of the signals except the portion of noise.

The bio-information measurer 1030 may extract feature points from the obtained oscillometric waveform, and may measure bio-information by applying the extracted feature points to a bio-information measurement model. For example, the bio-information measurer 1030 may extract, as feature points for measuring blood pressure, a contact pressure value at a maximum peak point of the oscillometric waveform, and contact pressure values which are at points to the left and right of the maximum peak point and have 0.5 to 0.7 of the value at the maximum peak point.

Upon measuring bio-information, the bio-information measurer 1030 may control an output module to provide the measured bio-information, the measured plurality of pulse wave signals, and/or the measured contact pressure values to a user. In this case, the output module may include a display module, a speaker, and/or a haptic device.

Figure 11:
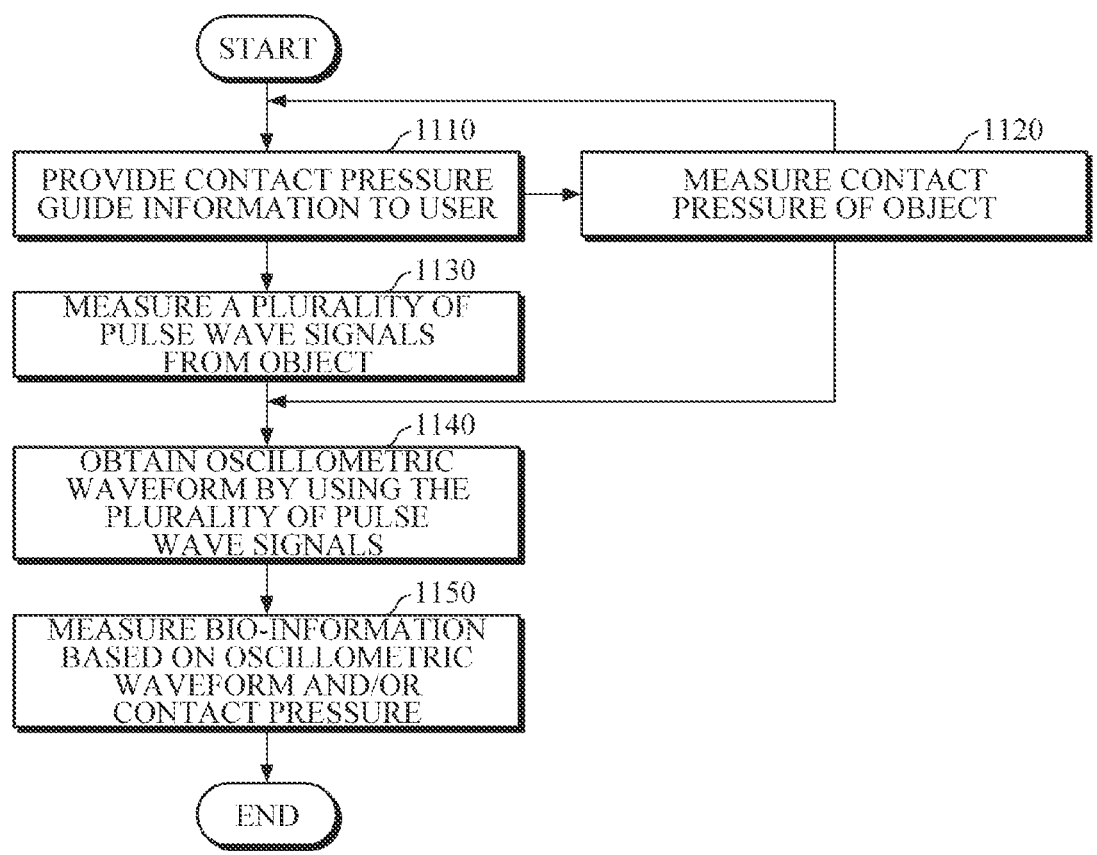
FIG. 11 is a flowchart illustrating a bio-information measuring method according to another exemplary embodiment.

FIG. 11 is a flowchart illustrating a bio-information measuring method according to another exemplary embodiment.

The bio-information measuring method of FIG. 11 is an example of a bio-information measuring method performed by the bio-information measuring apparatus 900 of FIG. 9, which is described above in detail with reference to FIGS. 9 and 10, such that description thereof will be made briefly below.

Upon receiving a request for measuring bio-information, the bio-information measuring apparatus 900 may provide contact pressure guide information to a user in operation 1110. In this case, the contact pressure guide information may include a pressure value to be increased or decreased by a user for a pulse wave sensor, and/or a user's action information for inducing a change in pressure, and may be provided using various visual or non-visual methods.

While the pulse wave sensor measures pulse waves, a contact pressure sensor embedded in the bio-information measuring apparatus 900 may measure contact pressure between the pulse wave sensor and the object in operation 1120. Based on the measured contact pressure values, the bio-information measuring apparatus 900 may continuously provide the contact pressure guide information while the pulse wave sensor measures the pulse waves in operation 1110.

The pulse wave sensor may measure a plurality of pulse wave signals from an object, for which bio-information is to be measured, for a predetermined period of time in operation 1130. In this case, the plurality of pulse wave signals may be signals having different wavelengths.

The providing of the contact pressure guide information in operation 1110, the measuring of the contact pressure in operation 1120, and the measuring of the pulse wave signals in operation 1130 are not performed in time-sequential order, but may be performed at the same time for a predetermined period of time.

Then, the bio-information measuring apparatus 900 may obtain an oscillometric waveform by using the measured plurality of pulse wave signals in operation 1140. For example, the bio-information measuring apparatus 900 may obtain a quadratic differential signal by performing quadratic differentiation on the plurality of pulse wave signals, and may obtain the oscillometric waveform by using the obtained quadratic differential signal. The bio-information measuring apparatus 900 may subtract a short-wavelength signal from a long-wavelength signal among the quadratic differential signals, and may obtain the oscillometric waveform based on the measured contact pressure.

Subsequently, the bio-information measuring apparatus 900 may measure bio-information based on the obtained oscillometric waveform in operation 1150. In this case, the bio-information measuring apparatus 900 may extract feature points from the oscillometric waveform, and may measure bio-information by applying the extracted feature points to a bio-information estimation model.

Figure 12:
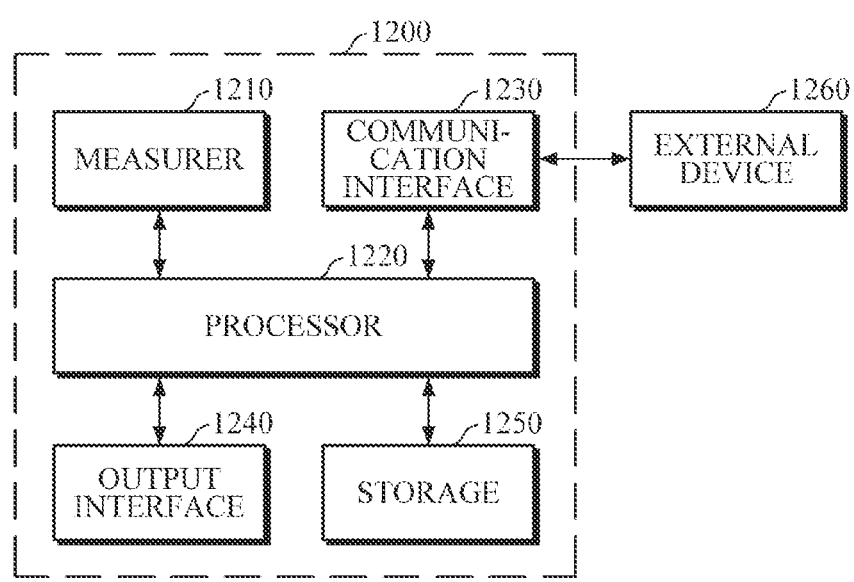
FIG. 12 is a block diagram illustrating a bio-information measuring apparatus according to an exemplary embodiment.

FIG. 12 is a block diagram illustrating a bio-information measuring apparatus according to another exemplary embodiment.

Referring to FIG. 12, the bio-information measuring apparatus 1200 includes a measurer 1210, a processor 1220, a communication interface 1230, an output interface 1240, and a storage 1250.

The measurer 1210 may include a pulse wave sensor to measure pulse wave signals from an object. In addition, the measurer 1210 may further include a contact pressure sensor to measure contact pressure between the pulse wave sensor and the object while the pulse wave sensor measures the pulse wave signals from the object.

The processor 1220 may control other parts 1210, 1230, 1240, and 1250 of the bio-information measuring apparatus 900, and may process various functions based on a performance result of the other parts 1210, 1230, 1240, and 1250.

For example, upon receiving a request for measuring bio-information, the processor 1220 may control the measurer 1210 to measure pulse wave signals and/or contact pressure signals. Further, once the pulse wave signals and/or the contact pressure signals are measured, the processor 1220 may measure bio-information based on the measured pulse wave signals and/or contact pressure signals. In this case, the measured pulse wave signals may be a plurality of pulse wave signals having different wavelengths. The processor 1220 may obtain an oscillometric waveform based on a difference signal, obtained by subtracting a short-wavelength pulse wave signal from a long-wavelength pulse wave signal, and/or based on the contact pressure signal, and may measure bio-information based on the obtained oscillometric waveform.

Further, the processor 1220 may control the output interface 1240 to provide the measured pulse wave signals, the contact pressure signals, or a measurement result of bio-information to a user. The output interface 1240 may be controlled by the processor 1220 to display information on a display module, and to output information by non-visual methods, such as voice, vibrations, and/or tactility, using a speaker module and a haptic module.

In addition, the processor 1220 may store the measured pulse wave signals, the contact pressure signals, or the measurement result of bio-information in a storage 1250. Moreover, the processor 1220 may measure bio-information by referring to reference information stored in the storage 1250. In this case, the reference information may include a bio-information measurement model and/or user characteristic information. The processor 1220 may store reference information received from an external device 1260 through the communication interface 1230, reference information input by a user, or the like in the storage 1250.

In this case, the storage 1250 may include at least one storage medium of a flash memory type memory, a hard disk type memory, a multimedia card micro type memory, a card type memory (e.g., an SD memory, an XD memory, etc.), a Random Access Memory (RAM), a Static Random Access Memory (SRAM), a Read Only Memory (ROM), an Electrically Erasable Programmable Read Only Memory (EEPROM), a Programmable Read Only Memory (PROM), a magnetic memory, a magnetic disk, and/or an optical disk.

Further, the processor 1220 may control the communication interface 1230 to be connected to the external device 1260, and may perform necessary functions. In this case, the external device 1260 may include a smartphone, a tablet PC, a laptop computer, a desktop computer, and/or a cuff-type blood pressure measuring apparatus, but is not limited thereto.

For example, upon measuring bio-information, the processor 1220 may transmit a measurement result of bio-information to the external device having relatively excellent computing performance, to provide the information to a user through an output module of the external device 1260, and may manage a history of various types of bio-information. Alternatively, the processor 1220 may receive a cuff pressure value from a cuff-type blood pressure measuring apparatus, and may compare the received cuff pressure value with a measurement result of bio-information, to provide a result of the comparison to a user.

Upon receiving a control signal from the processor 1220, the communication interface 1230 may access a communication network by using a communication technique to be connected to the external device 1260, and may transmit and receive necessary information with the external device 1260. Examples of the communication technique may include Bluetooth communication, Bluetooth Low Energy (BLE) communication, Near Field Communication (NFC), WLAN (Wi-Fi) communication, Zigbee communication, Infrared Data Association (IrDA) communication, Wi-Fi Direct (WFD) communication, Ultra-Wideband (UWB) communication, Ant+ communication, WIFI communication, Radio Frequency Identification (RFID) communication, Wi-Fi communication, and mobile communication. However, this is merely exemplary and is not intended to be limiting.

Figure 13A:
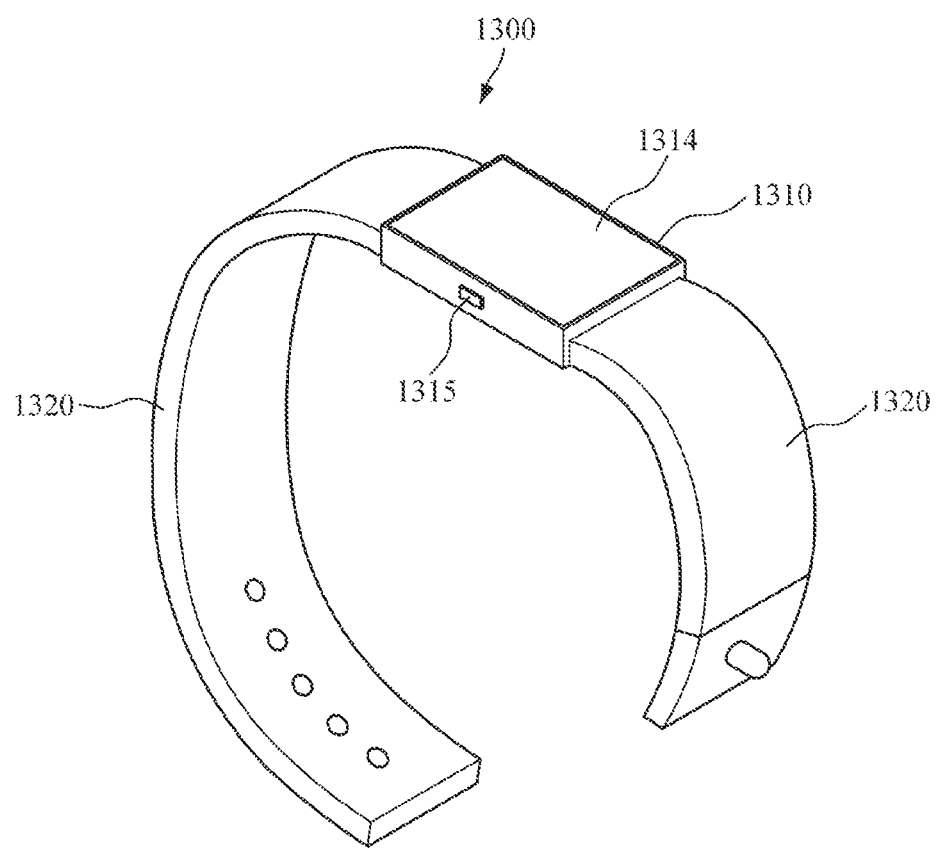
FIGS. 13A and 13B are diagrams illustrating a wearable device according to an exemplary embodiment.
Figure 13B:
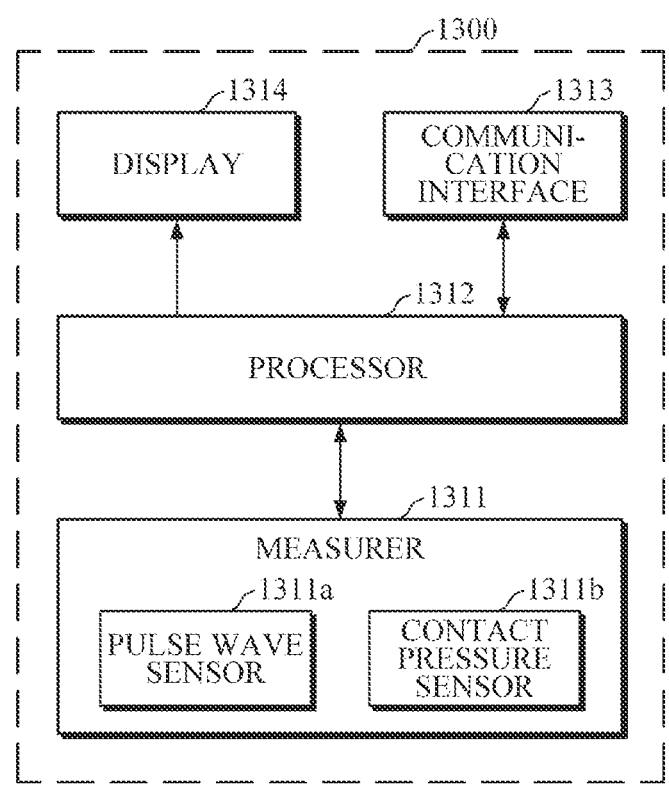

FIGS. 13A and 13B are diagrams illustrating a wearable device according to another exemplary embodiment. Various embodiments of the above-described bio-information measuring apparatus may be mounted in a smart watch or a smart band-type wearable device which is wearable on a wrist as illustrated herein. However, the wearable device is merely an example used for convenience of explanation, and it should not be construed that application of the embodiments is limited to a smart watch or a smart band-type wearable device.

Referring to FIGS. 13A and 13B, the wearable device 1300 includes a main body 1310 and a strap 1320.

The strap 1320 may be flexible, and may be connected to both ends of the main body 1310 to be bent around a user's wrist or may be bent in a manner which allows the strap 1320 to be detached from a user's wrist. Alternatively, the strap 1320 may be formed as a band that is not detachable. In this case, air may be injected into the strap 1320 or an airbag may be included in the strap 1320, so that the strap 1320 may have elasticity according to a change in pressure applied to the wrist, and the change in pressure of the wrist may be transmitted to the main body 1310.

A battery, which supplies power to the wearable device 1300, may be embedded in the main body 1310 or the strap 1320.

Further, the wearable device 1300 includes a measurer 1311 to measure a bio-signal from an object, and a processor 1312 to obtain bio-information of the object based on the bio-signal.

The measurer 1311 may be mounted at a bottom portion of the main body 1310, i.e., a portion that comes into contact with an object (e.g., a user's wrist) and may measure a bio-signal from the object according to a control signal of the processor 1312. The measurer 1311 includes a pulse wave sensor 1311a to measure a pulse wave signal from an object, and a contact pressure sensor 1311b to measure a contact pressure signal between the pulse wave sensor 1311a and the object. The pulse wave sensor 1311a may be mounted at the bottom of the main body 1310 to be exposed to the object, and the contact pressure sensor 1311b may be mounted in the main body 1310 at a position which is relatively further from the object when compared to the pulse wave sensor 1311a.

The pulse wave sensor 1311a may include one or more light sources to emit light onto the object, and one or more detectors to detect light emanating from the object, and may measure a plurality of pulse wave signals, having different wavelengths, from the object. In this case, various exemplary embodiments of the pulse wave sensor 1311a for measuring a plurality of pulse wave signals having different wavelengths are described above with reference to FIGS. 2A to 2C.

The contact pressure sensor 1311b and the pulse wave sensor 1311a may be mounted in the main body 1310. For example, the contract pressure sensor 1311b and the pulse wave sensor 1311a may be disposed side-by-side on the same surface of the main body 1310. The contact pressure sensor 1311b may measure contact pressure between the pulse wave sensor 1311a and the object while the pulse wave sensor 1311a measures pulse wave signals from the object. In measuring the contact pressure between the pulse wave sensor 1311a and the object, the contact pressure sensor 1311b may measure a contact pressure between the contact pressure sensor 1311b itself and the object, and may determine the contact pressure between the contact pressure sensor 1311b and the object as the contact pressure between the pulse wave sensor 1311a and the object. The contact pressure sensor 1311b may include a force sensor and an area sensor to calculate contact pressure by using values measured by these sensors, but the contact pressure sensor 1311b is not limited thereto.

For example, the contact pressure sensor 1311b may measure contact pressure of the object, which is transmitted to the main body 1310 through the strap 1320 which is wrapped around the wrist to secure the main body 1310 to the object. In this case, a user may change contact pressure between the object and the pulse wave sensor 1311a by adjusting tension in the strap by changing a thickness of the wrist, on which the main body 1210 is worn, while the pulse wave signals.

In another example, a user may change contact pressure between the pulse wave sensor 1311a and the object by gradually increasing pressure while touching a display 1314 with a finger and the like, or by gradually decreasing pressure while strongly pressing the display 1314. In this case, the display 1314 may display guide information for changing contact pressure, such as pressing intensity of a user's finger while the pulse wave signals are measured. The guide information may include intensity of reference pressure, a position of a finger, and/or an actually measured contact pressure value. However, the change in contact pressure is not limited thereto, and the contact pressure may be changed by various methods.

The processor 1312 may generate a control signal to control the measurer 1311 according to a user's request. Further, the processor 1312 may receive the measured pulse wave signals and/or contact pressure signals which are measured by the measurer 1311, and may measure bio-information by using the received pulse wave signals and/or contact pressure signals. For example, the processor 1312 may start measuring the plurality of pulse wave signals in response to the contact pressure sensor 1311b detecting a gradual increase or decrease of a contact pressure. The processor 1322 may measure the plurality of pulse wave signals while controlling the display 1314 to display an image prompting the user to gradually increase or decrease his/her pressure exerted onto the contact pressure sensor 1311b. For example, the display 1314 may display a motion of a hand that clenches a fist so to induce the user to increase the contact pressure between the wrist and the wearable device 1300.

For example, the processor 1312 may obtain an oscillometric waveform by using the measured plurality of pulse wave signals and contact pressure signals, and may measure blood pressure by using oscillometry. For example, the processor 1312 may obtain a difference signal by subtracting a short-wavelength pulse wave signal from a long-wavelength pulse wave signal among the plurality of pulse wave signals, and may obtain the oscillometric waveform by using the obtained difference signal and the contact pressure signal. In this case, the processor 1312 may generate a differential signal by differentiating the plurality of pulse wave signals, and may obtain a difference signal by using the generated differential signal, in which the order of differentiation is not specifically limited. Upon obtaining the oscillometric waveform, the processor 1312 may extract feature points from the oscillometric waveform, and may measure blood pressure by applying the extracted feature points to a blood pressure estimation model.

Upon receiving a request for measuring bio-information from a user, the processor 1312 max provide contact pressure guide information so that a user may change contact pressure between the pulse wave sensor 1311a and the object by applying pressure to the main body. In this case, the contact pressure guide information may include a contact pressure value to be applied by a user, but is not limited thereto, and may include an action to be taken by a user to apply pressure to the main body.

Further, once the contact pressure sensor 1311b measures contact pressure between the pulse wave sensor 1311a and the object, the processor 1312 may provide feedback on contact pressure to a user based on the measured contact pressure. In this case, the user may apply pressure with appropriate intensity based on the contact pressure information provided as feedback.

The processor 1312 may store estimated bio-information (e.g., blood pressure history information and bio-signals used for measuring each blood pressure value, and/or feature points) in a storage device. In addition, the processor 1312 may generate additional information required for managing health of a user, such as alarm or warning information associated with the estimated bio-information, development of change in health state, and the like, and may manage the generated information in the storage device Further, the wearable device 1300 may include a manipulator 1315 and the display 1314 which are mounted at the main body 1310.

The manipulator 1315 may receive a control command of a user and may transmit the received control command to the processor 1312. The manipulator 1315 may include a power button for inputting a command to turn on/off the wearable device 1300.

The display 1314 may be controlled by the processor 1312 to provide various types of information associated with detected bio-information to a user. For example, the display 1314 may display additional information, such as the detected blood pressure, alarm information, warning information, and the like, to a user by using various visual/non-visual methods.

In addition, the main body 1310 may further include, in an internal space, a communication interface 1313 for communication with an external device such as a mobile terminal of a user.

The communication interface 1313 may be controlled by the processor 1312 to communicate with an external device of a user which has relatively excellent computing performance, and to transmit and receive necessary information. For example, the communication interface 1313 may receive a request for estimating bio-information from a mobile terminal of a user. Further, the communication interface 1313 may transmit extracted feature points or feature information to an external device to request estimation of bio-information. In addition, the communication interface 1313 may transmit an estimation result of bio-information to an external device to display the information to a user through a display having improved performance, or use the information for various purposes such as management of a bio-information history, disease research, and the like.

While not restricted thereto, an exemplary embodiment can be embodied as computer-readable code on a computer-readable recording medium. The computer-readable recording medium is any data storage device that can store data that can be thereafter read by a computer system. Examples of the computer-readable recording medium include read-only memory (ROM), random-access memory (RAM), CD-ROMs, magnetic tapes, floppy disks, and optical data storage devices. The computer-readable recording medium can also be distributed over network-coupled computer systems so that the computer-readable code is stored and executed in a distributed fashion. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A blood pressure measuring apparatus comprising:
   a pulse wave sensor configured to measure a plurality of pulse wave signals from an object, the plurality of pulse wave signals comprising a first pulse wave signal and a second pulse wave signal;
   a contact pressure sensor configured to measure a contact pressure between the blood pressure measuring apparatus and the object while the plurality of pulse wave signals are measured; and
   a processor configured to:
   obtain a difference signal by subtracting an n-th order differential signal of the second pulse wave signal from an n-th order differential signal of the first pulse wave signal, n being an integer equal to or greater than 1;
   obtain an oscillometric waveform based on the difference signal and the contact pressure; and
   obtain blood pressure using the oscillometric waveform,
   wherein the pulse wave sensor comprises:
   a first pulse wave sensor comprising a first light source configured to emit a of a first wavelength onto the object, and a first detector configured to measure the first pulse wave signal in response to the light of the first wavelength returning from the object; and
   a second pulse wave sensor comprising a second light source configured to emit a light of a second wavelength, which is different from the first wavelength, onto the object, and a second detector configured to measure the second pulse wave signal in response to the light of the second wavelength returning from the object,
   wherein the first wavelength is longer than the second wavelength, and
   wherein the processor is further configured to provide contact pressure guide information to a user while the plurality of pulse wave signals are measured.

2. The blood pressure measuring apparatus of claim 1, wherein the processor is further configured to normalize the first pulse wave signal and the second pulse wave signal, and obtain the difference signal based on the normalized first pulse wave signal and the normalized second pulse wave signal.

3. The blood pressure measuring apparatus of claim 1, wherein the processor is further configured to exclude a portion, where noise occurs, from the plurality of pulse wave signals based on the contact pressure.

4. The blood pressure measuring apparatus of claim 1, further comprising an output interface configured to provide at least one of the measured plurality of pulse wave signals, the measured contact pressure, the contact pressure guide information, and a measurement result of blood pressure to the user.

5. The blood pressure measuring apparatus of claim 1, further comprising a communication interface configured to transmit at least one of the plurality of pulse wave signals and the blood pressure to an external device.

6. The blood pressure measuring apparatus of claim 1, wherein the processor comprises a sensor controller configured to sequentially switch on the first light source and the second light source based on driving conditions of the first light source and the second light source.

7. The blood pressure measuring apparatus of claim 1, further comprising a storage configured to store driving conditions comprising at least one of a driving order and a driving time of the first light source and the second light source.

8. The blood pressure measuring apparatus of claim 1, wherein each of the first detector and the second detector comprises a color filter configured to pass a predetermined wavelength band.

9. A blood pressure measuring method that is performed by a blood pressure measuring apparatus, the blood pressure measuring method comprising:
   by a first pulse wave sensor, measuring a first pulse wave signal from an object, the first pulse wave sensor comprising a first light source configured to emit a light of a first wavelength onto the object, and a first detector configured to measure the first pulse wave signal in response to the light of the first wavelength returning from the object;
   by a second pulse wave sensor, measuring a second pulse wave signal from the object, the second pulse wave sensor comprising a second light source configured to emit a light of a second wavelength, which is different from the first wavelength, onto the object, and a second detector configured to measure the second pulse wave signal in response to the light of the second wavelength returning from the object;

providing contact pressure guide information to a user while the first pulse wave signal and the second pulse wave signal are measured;

measuring a contact pressure between the blood pressure measuring apparatus and the object while the first pulse wave signal and the second pulse wave signal are measured;

obtaining a difference signal by subtracting an n-th order differential signal of the second pulse wave signal from an n-th order differential signal of the first pulse wave signal, n being an integer equal to or greater than 1;

obtaining an oscillometric waveform based on the difference signal and the contact pressure; and obtaining blood pressure using the oscillometric waveform, wherein the first wavelength is longer than the second wavelength.

10. The blood pressure measuring method of claim 9, further comprising normalizing the first pulse wave signal and the second pulse wave signal, and obtaining the difference signal based on the normalized first pulse wave signal and the normalized second pulse wave signal.

11. The blood pressure measuring method of claim 9, wherein the obtaining the oscillometric waveform comprises excluding a portion, where noise occurs, from the first pulse wave signal and the second pulse wave signal based on the contact pressure.

12. The blood pressure measuring method of claim 9, further comprising by an output interface, providing at least one of the first pulse wave signal, the second pulse wave signal, the contact pressure, the contact pressure guide information, and a measurement result of the blood pressure to the user.

* * * * *